United States Patent [19]

Mitchnick et al.

[11] Patent Number: 5,733,531

[45] Date of Patent: *Mar. 31, 1998

[54] COMPOSITE UV SUNBLOCK COMPOSITIONS

[75] Inventors: Mark A. Mitchnick, Wainscott, N.Y.; Garry T. Gwozdz, Nazareth; Fortunato J. Micale, Bethlehem, both of Pa.

[73] Assignees: SunSmart, Inc., Wainscott, N.Y.; Sibmicro Encapsulation Technologies, Inc., Bethlehem, Pa.

[*] Notice: The term of this patent shall not extend beyond the expiration date of Pat. No. 5,223,250.

[21] Appl. No.: 251,740

[22] Filed: Jun. 1, 1994

Related U.S. Application Data

[63] Continuation-in-part of Ser. No. 231,567, Apr. 22, 1994, abandoned, which is a continuation-in-part of Ser. No. 101,661, Aug. 4, 1993, Pat. No. 5,587,148, which is a continuation of Ser. No. 704,250, May 22, 1991, abandoned, which is a continuation-in-part of Ser. No. 651,696, Feb. 5, 1991, Pat. No. 5,223,250.

[51] Int. Cl.$^6$ ............................ A61K 7/42; A61K 7/44; A61K 9/10; A61K 9/14

[52] U.S. Cl. .................. 424/59; 424/60; 424/63; 424/64; 424/400; 424/401; 514/844; 514/847; 514/938

[58] Field of Search ..................... 424/59, 60, 63, 424/64, 400, 401; 514/844, 847, 938

[56] References Cited

U.S. PATENT DOCUMENTS

| | | | |
|---|---|---|---|
| 4,247,411 | 1/1981 | Vanlerberghe et al. | 252/316 |
| 4,804,531 | 2/1989 | Grollier | 424/47 |
| 4,935,246 | 6/1990 | Ahrens | 424/490 |
| 5,028,417 | 7/1991 | Bhat et al. | 424/59 |
| 5,223,250 | 6/1993 | Mitchell et al. | 424/59 |
| 5,244,665 | 9/1993 | Natraj et al. | 424/401 |
| 5,270,055 | 12/1993 | Moest | 424/476 |

FOREIGN PATENT DOCUMENTS

| | | | |
|---|---|---|---|
| 7247566 | 10/1971 | Austria | A61L 23/00 |
| 2622441 | 10/1988 | France | A61K 7/42 |
| 2646346 | 4/1989 | France | A61K 7/42 |
| 7098205 | 6/1982 | Japan | A61K 7/02 |
| 0184004 | 9/1985 | Japan | A61K 7/00 |
| 2184356 | 12/1986 | United Kingdom | A61K 7/42 |

*Primary Examiner*—Shelley A. Dodson
*Attorney, Agent, or Firm*—Kathleen M. Williams

[57] ABSTRACT

The invention encompasses topical sunblock formulae for shielding skin from ultraviolet radiation, and a composite sunblocking component thereof. The sunblocking component of the formula includes an effective amount of a plurality of particles having diameters in the range of about 0.01–100 microns, each particle including a matrix and a UV-attenuating compound incorporated into the matrix. The composite sunblocking component may include a particle that is colored or transparent, depending upon the matrix, UV-attenuating compound and the particle size. The sunblocking component is dispersible in water and thus in water-based dermatological carriers. The formula includes these particles dispersed within a dermatologically acceptable liquid carrier in at least an amount sufficient to shield substantially all of the skin over which the formula is applied from hazardous effects of ultraviolet radiation.

25 Claims, No Drawings

COMPOSITE UV SUNBLOCK COMPOSITIONS

This application is a continuation-in-part of U.S. Ser. No. 08/231,567, filed Apr. 22, 1994 now abandoned, which is a continuation-in-part of 08/101,661, filed Aug. 4, 1993 now U.S. Pat. No. 5,587,148, which is a continuation of U.S. Ser. No. 07/704,250, filed May 22, 1991, now abandoned, which is a continuation-in-part of U.S. Ser. No. 07/651,696, filed Feb. 5, 1991, now U.S. Pat. No. 5,223,250.

FIELD OF THE INVENTION

The present invention relates generally to particulate materials adapted for use as sunblocking agents and more particularly to the use of these materials in transparent or colored, cosmetically acceptable UV sunscreen products, as well as in improved cosmetic formulations having an increased ability to protect the user from UV radiation.

BACKGROUND OF THE INVENTION

One portion of the solar spectrum comprises wavelengths of electromagnetic energy which range between about 290 and 3,000 nanometers (nm). This range may be divided into different regions, namely: (1) the ultraviolet region (290–400 nm), (2) the visible region (400–760 nm) and (3) the near-infrared region (>760 nm). The ultraviolet region has, moreover, been arbitrarily divided into three bands, referred to as the UVA, UVB and UVC bands.

The UVB band extends from 290 to 320 nm. It is the principal cause of the sunburn reaction and it is also the most effective in stimulating the tanning reaction in the skin. UVC radiation (200– 290 nm) from the sun does not reach the surface of the earth, although one can encounter radiation in this range from artificial sources such as germicidal lamps and high and low pressure mercury arc lamps. For purposes of the present invention, however, protection against UVC radiation is generally not a major concern, i.e., in contrast to the dangers posed by UVA and UVB radiation. The UVA band, which extends from 320–400 nm, can also cause the tanning reaction. UVA radiation can also cause sunburns, but its capacity to do so is less than that of UVB radiation.

The amount of UVA radiation exposure, however, is increasing. This is due to the fact that most sunscreens effectively block only UVB radiation. As stated above, UVB radiation is more capable than UVA radiation of causing the tanning and burning reactions. Therefore, if one is using a sunscreen that blocks UVB radiation he/she will tend to stay in the sun for an extended period of time because the immediate effects of the sun tan/burn are not evident. The problem is that UVA is still penetrating the skin and although it is not causing any immediately obvious effects, it is causing long term damage. In recent years, it has been well documented that UVA radiation, like UVB radiation, is harmful to the skin. In fact, current data reveal that solar radiation containing these wavelengths (A and B) is a contributing cause of skin cancer, which presently accounts for 30–40% of all new cancers each year. In the United States alone, 500,000 new cases of skin cancer will be reported this year and the number is expected to keep rising in the future. UVA radiation has been shown to promote skin cancer by inhibiting enzymes that repair cells damaged by UVB radiation. UVA radiation also penetrates more deeply into the skin than UVB radiation and causes changes in blood vessels and premature aging of the skin, thus adding to the damage produced by UVB rays (see, e.g., Hurwitz, Sidney, "The Sun and Sunscreen Protection: Recommendations for Children", Dermatol Surg. Oncol; 14:6(June 1988) p. 657). The goal of any sunscreen should thus be to protect the user from both UVA and UVB radiation with a minimum of side effects. This end has not been adequately achieved with the use of presently available sunscreen products.

Topical sunscreen products can be grouped into two broad categories, i.e., organic and inorganic (physical) sunscreens.

Commercially available sunscreen products contain from about 3 to about 26% of one or more UV absorbing chemicals. When applied to the surface of the skin as a thin film, i.e., about 10–15 μm in thickness, these chemicals act as a filter to diminish the penetration of UV radiation to the cells of the epidermis. These sunscreens are typically applied in a cream, oil, lotion, alcohol or gel vehicle and they are usually colorless because they do not contain any visible light-absorbing chemicals. The most widely used organic-based sunscreens contain, for example, paraaminobenzoic acid (PABA), PABA esters (glyceryl PABA), amyldimethyl PABA and octyldimethyl PABA), benzophenones (oxybenzone and sulisobenzone), cinnamates (octylmethoxy cinnamate and cinoxate), salicylates (homomethyl salicylate), anthranilates such as menthyl anthranilate, 2-ethylhexyl-2-cyano-3,3-diphenyl acrylate, 2-phenyl benzimidazole-5-sulfonic acid, digalloyl trioleate, 3-(4-methyl benzylidene) camphor, 4-isopropyl dibenzoyl methane, butyl methoxy dibenzoyl methane, 2-ethyl-2-cyano-3,3'-diphenyl acrylate. To date, more than twenty-one such chemicals have been approved by the United States Food and Drug Administration as "safe and effective" agents in protecting skin against sunburn (see, e.g., Pathak, Madhu, "Sunscreens: Topical and Systemic Approaches for Protection of Human Skin Against Harmful Effects of Solar Radiation", Continuing Medical Education Series, J. Am. Acad. Dermat., 7:3 (September 1982) p. 285,291).

Questions have recently been raised, however, by the medical profession as to whether the organic chemical components of these sunscreens are indeed inert and further, whether repeated use of such sunscreens can result in significant transdermal absorption of these chemicals. Because chemical sunscreens are applied topically in relatively high concentrations (i.e., up to 26%), contact and photocontact sensitization can occur, as well as hypersensitivity, i.e., photoallergic reactions (see Drumgoogle et al., "Sunscreening Agent Intolerance: Contact and Photocontact Sensitization and Contact Urticania", J. Am. Acad. Dermatol., 1990:22, p. 1068).

Physical or inorganic sunscreens, on the other hand, comprise particles of a relatively physiologically inert sunblock, i.e., UV-absorbing, compound typically suspended in a cream or lotion. Materials frequently utilized for this purpose include kaolin, talc and two metal oxides, i.e., titanium dioxide and zinc oxide. The latter two compounds are not associated with the inflammatory reactions noted above.

The physical sunscreen products are, however, typically messy and occlusive. Moreover, they additionally form a visible, colored (e.g., white) layer on the surface of the skin which is cosmetically unacceptable to many who are in need of sunscreen protection. This causes many such individuals to forego the use of these products. The color of these compositions is attributable to the optical properties of the particles from which these materials are formed. These properties are at least partially dependent upon the size of these particles, which typically have a diameter of >250 nm (i.e., 0.25 microns).

In addition, presently available physical sunscreens are not easily washed off of the user's body. Instead, the base typically "melts" off with the heat of the sun, thus incidentally staining or otherwise discoloring the user's clothing. Moreover, because they are applied as relatively thick films, i.e., greater than 10 µm, use of these products may also promote undesirable skin conditions, including miliaria, a skin disease caused by an inflammation of the sweat glands, and folliculitis, an inflammation of the hair follicle. As such, these physical sunscreen products are deemed cosmetically unacceptable by a large class of image conscious persons, which primarily includes young people. Unfortunately, this same group is the exact population that needs solar protection the most. It has been stated that proper use of sunscreens prior to the age of 18 would prevent 80% of skin cancers (see, e.g., Taylor et al., "Photoaging/Photodamage and Photoprotection", 22 J. Am. Acad. Dermatol., 9 (1990).

In one variant of the "typical" prior art physical sunblocks described above, certain commercial sunscreen products containing titanium dioxide are made with what is known as "micronized" or "large surface area" particles of the metal oxide. These particles have a diameter an order of magnitude smaller (i.e., measuring about 0.01–0.1µ) than the "standard" pigment-grade sized particles (measuring about 0.25µ) described above.

Greater public awareness of the harmful effects of exposure to excessive solar radiation has therefore resulted in an increased use of sunscreen products by the public, coupled with a call for improved sunscreen materials free of the drawbacks described above by those whose livelihood and/or leisure activities cause them to be exposed to any substantial amounts of solar radiation.

It is thus an object of the invention to provide new, improved cosmetically acceptable physical sunblock materials capable of attenuating a greater degree of ultraviolet radiation so as to prevent the user's skin from being damaged by exposure to these solar rays.

It is a further object of the invention to provide sunscreen products utilizing sunblocks of the type described above which are capable of effectively attenuating UVA and UVB radiation while retaining a substantially visibly clear or a having colored appearance, if desired, upon the surface of the skin.

It is still further object of the invention to provide physical sunblocks which do not cause adverse chemical reactions upon the skin of the user.

It is another object of the invention to provide a physical sunblock component which does not interact with other formulation ingredients.

It is another object of the invention to provide a variety of improved cosmetic formulations containing the particulate sunblock materials described herein which offer an enhanced degree of solar protection to the user.

It is a further object of the invention to provide an inherently non-water-soluble organic sunscreen component that is not restricted to use in an oil phase of a sunscreen emulsion.

Yet another object of the invention is to provide a sunscreen component that is miscible with a water-based sunscreen; for example, to adapt previously oil-based sunscreen components for use in a water-based sunscreen.

Another object of the invention is to adapt a sunscreen component to make it water-dispersible.

Yet another object of the invention is to adapt a sunscreen component to minimize undesirable chemical reactions between the component and other active ingredients in the sunscreen formula.

A further object of the invention is to provide for facile preparation of a sunscreen component by avoiding the use undesirable chemicals, e.g., solvents, in the manufacture process.

Another object of the invention is to increase the efficacy of the sunscreen; that is, to confer a higher sun protection factor than is available from conventional sunscreens using approximately the same volume.

Yet another object of the invention is to provide a particle having an encapsulating component that promotes film formation, thereby causing the particle to adhere to the skin and confer a waterproof quality to the sunscreen.

SUMMARY OF THE INVENTION

A first embodiment of the invention is directed to the formation of sunscreen products comprising a plurality of small capsules or particles, the particles having diameters in the range of approximately 0.01 to 100 microns, and preferably 0.01 to 50 or 0.01 to 20 microns, containing one or more UV-attenuating (i.e., UV-absorbing or -reflecting) compounds. Preferably, the capsule confers a visibly clear quality to the sunscreen as applied to the skin; however, color additives may be added to the particles to confer a color quality to the sunscreen as applied to the skin. Preferably, the capsule is spherical. Preferably, the average diameter of the particles in a plurality of particles is 0.5–50, and most preferably 1–10 microns.

Thus, the invention features a component of a sunblock formula comprising a plurality of particles, having diameters in the range of about 0.01–100 microns, formed from a matrix and at least one UV-attenuating compound incorporated into the matrix, the particles being dispersible within a substantially transparent dermatologically acceptable liquid carrier.

A sunscreen component of the invention is distinguishable over prior art sunscreen components in several respects. For example, sunscreen particles of the invention are dispersible in water and thus in water-based dermatological carriers, even particles containing UV-attenuating components that are inherently difficult to disperse by virtue of certain surface properties. For example, the particles may be composed of an oil-soluble material that is not water-soluble but for the encapsulating matrix; i.e., the oil-solubilizing properties are masked by the encapsulating matrix, rendering the encapsulated material dispersible in water.

The sunscreen component also is distinguishable over prior art sunscreen components in that it is prepared according to a manufacture process that does not require the use of an intermediate organic solvent, and thus both the manufacture process and the sunscreen product are completely free of such solvents. That is, a water-dispersible sunscreen component is provided according to the invention without such highly toxic and thus undesirable chemicals. The level of organic solvents present in the water-dispersible sunscreen components described herein are substantially lower than those found in the prior art sunscreen components that are made using solvent-extraction methods of manufacture, where toxicity is a concern. Applicants' encapsulated sunscreen components have exceedingly low, i.e., undetectable levels, of organic solvents and are therefore referred to in the present specification as "solvent-free".

Thus, an important advantage of the encapsulated sunscreen components of the invention is found in their safety and ease of manufacture. The sunscreen components achieved via solvent-free methods of manufacture are also less toxic than solvent-synthesized components, an important consideration for agents applied to the skin. This solvent-free material is thus suitable for application to human skin since the solvent content is present at undetectable levels and thus is not likely to cause dangerous effects in humans.

A preferred encapsulating matrix useful according to the invention comprises wax. As used herein, "wax" refers to a natural or synthetic material having the following characteristics; i.e., it is essentially non-water soluble (i.e., <5%); it has a melting point preferably below 100 degrees but not above 200 degrees Centigrade; and it has a viscosity of less than 500 cp. at a temperature less than 100 degrees Centigrade. The invention encompasses the use of an encapsulating material that does not possess these characteristics alone but is combinable with another material to produce a mixture having all of these characteristics. Waxes include, but are not limited to, natural and synthetic waxes that contain mixtures of alkyl wax esters, resins, and other vegetable matter components; clay-treated microcrystalline waxes; oxidized hydrocarbon waxes; natural and synthetic beeswax, auto-oxidized beeswax, candelilia, carnauba, and synthetic waxes prepared by esterification of natural plant-derived fatty acids and alcohols; various grades of paraffin waxes; and natural and synthetic oils.

Other preferred matrices include but are not limited to materials that are encapsulators according to a solvent-free process, e.g., polymeric materials such as alkylated vinyl pyrrolidone polymers; long chain alcohols; long chain carboxylic acids; propylene glycol ester of fatty acids; ethene homopolymers; various grades of polymerized alkenes and alpha alkenes with molecular weights greater than 100 g/mole; ethylene-acrylic acid copolymers; ethylene-vinyl acetate copolymers; and lipid and protein-derivatives.

These preferred matrices have the additional advantage of being inexpensive and relatively non-toxic, as they are commonly-used cosmetic ingredients.

Optimally, the UV-attenuating compound is encapsulated within the matrix particle such that, upon admixture of the UV-attenuating compound-encapsulated particles with a sunscreen emulsion, the UV-attenuating compound does not substantially contact the surrounding emulsion or the skin. Alternatively, the UV-attenuating compound may be combined with the matrix in formation of the particle such that the compound is substantially evenly-distributed throughout the matrix.

Thus, the invention also includes a sunscreen formula comprising two or more UV-attenuating compounds, each compound individually encapsulated in the matrix to form a first plurality of particles comprising a first encapsulated UV-attenuating compound and a second plurality of particles comprising a second encapsulated UV-attenuating compound, etc. When formulating a sunscreen formula, any given ratio of the first or second plurality of particles may be combined in the sunscreen formula to provide an effective amount of sunblock.

Alternatively, the invention encompasses first and second UV-attenuating compounds that are together encapsulated in the matrix. The first and second UV-attenuating compounds may be organic or inorganic sunscreen agents. Organic agents include but are not limited to chemical sunscreens such as benzophenones, PABA and PABA derivatives, cinnamates, salicylates, anthranilates such as menthyl anthranilate, 2-ethylhexyl-2-cyano-3,3-diphenyl acrylate, 2-phenyl benzimidazole-5-sulfonic acid, digalloyl trioleate, 3-(4-methyl benzylidene) camphor, 4-isopropyl dibenzoyl methane, butyl methoxy dibenzoyl methane, 2-ethyl-2-cyano-3,3'-diphenyl acrylate. Inorganic agents include but are not limited to kaolin, talc, titanium dioxide, and zinc oxide.

Of course, it is to be understood that the invention encompasses a sunscreen formula comprising particles containing not only first and second UV-attenuating compounds, but also, if desired, third, fourth and fifth, etc. UV-attenuating compounds, whether the multiple UV-attenuating compounds be individually encapsulated or encapsulated in combinations.

The invention thus also provides a method of preparing the sunscreen component described above, comprising subjecting the matrix and the UV-attenuating compound to a solvent-free process to produce a solvent-free plurality of particles comprising the matrix and the UV-attenuating compound.

Additional advantages of the invention include providing an encapsulated organic sunscreen component that, by virtue of its inert encapsulating exterior is not restricted to use in the oil phase of a sunscreen emulsion. Thus, the encapsulated sunscreen component will be dispersible in a water-based sunscreen, if desired. Inherently oil-soluble sunscreen components may thus be adapted for use in a water-based sunscreen, and thus may be rendered water-dispersible. In addition, a toxic sunscreen component may be rendered less toxic or non-toxic via encapsulation according to the invention. Also, the use of encapsulated sunscreen components will minimize the undesirable chemical reactions between the component and other active ingredients in the sunscreen formula. Thus, ambient conditions around the sunscreen component itself within the sunscreen formula may be controlled by the presence of the encapsulating substance, regardless of the activities of additional components in the sunscreen formula. Another important advantage of the invention is that an encapsulated sunscreen provides a higher sun protection factor than an unencapsulated active sunscreen agent, when applied at the same concentrations.

In another aspect, the invention provides a process for preparing a component of a sunscreen formula, comprising the steps of: (a) heating an encapsulating matrix above its melting point at a temperature in the range of 30–200 degrees Centigrade to form a liquified, i.e., molten, encapsulating matrix; (b) mixing a UV attenuating compound with the liquified encapsulating matrix; (c) emulsifying the mixture of step (b) with an aqueous medium comprising a surfactant, the aqueous-medium being at a temperature in the range of 30–200 degrees Centigrade upon emulsification, such that the emulsion drop size is in the range of about 0.01–100 microns; and (d) cooling the emulsion to room temperature, wherein the particles formed therefrom have diameters in the range of about 0.01–100 microns and comprise the matrix in combination with the UV-attenuating compound, the particles being solvent-free and dispersible within a dermatologically acceptable carrier.

In preferred embodiments, the temperature range of steps (a) and (c), individually, is 30–100 degrees Centigrade; the encapsulating matrix comprises a substance selected from the group consisting of: natural wax and synthetic wax; the natural waxes comprising a material selected from the group consisting of alkyl wax esters, resins, and other vegetable matter components; clay-treated microcrystalline waxes; oxidized hydrocarbon waxes; natural and synthetic beeswax, auto-oxidized beeswax, candelilia, carnauba; the synthetic waxes comprising a material selected from the group consisting of synthetic waxes prepared by esterification of natural plant-derived fatty acids and alcohols; various grades of paraffin waxes.

In other preferred embodiments, the UV-attenuating compound is an organic or inorganic UV-attenuator; the inorganic UV-attenuator is pretreated with a hydrophobic compound prior to mixing with the heated encapsulating matrix; the organic sunscreen material is admixed with a solubilizing agent prior to incorporation into the matrix in an amount sufficient to reduce the potential of the UV-attenuator to recrystallize in the particle form.

In a second embodiment, the invention is directed to a sunscreen formulation comprising microfine particles of a zinc oxide sunblock suspended in a dermatologically suitable liquid carrier, preferably in the form of an emulsion. These micronized particles, as now produced by applicants, are formed using known techniques, such that the resultant particles have acceptable, i.e., reduced, levels of trace metals such as cadmium, arsenic, mercury, lead, etc., which levels are set forth in Table I below. These levels are substantially lower than those found in the particles described above for use in the rubber industry where toxicity is not a concern. Applicants' particles, having the requisite levels of these trace metals for use in the present invention, are therefore referred to in the present specification as substantially "pure". This substantially "pure" material is thus suitable for application to human skin since the trace metal content is maintained at or below the levels set forth in Table I below, that is, below levels which are likely to cause dangerous effects in humans.

Zinc oxide particles of the size and morphology described below, with such reduced levels of trace metal contamination, have not been previously known in the art, as far as applicants are aware. There has, in fact, been no call for this substantially pure form of zinc oxide since, as described herein, the use of this visually transparent UV-sunblock material was not previously contemplated by those working in the sunscreen or the cosmetic fields.

In a preferred embodiment, applicants' substantially pure zinc oxide particles are formed having a substantially spherical shape. This shape is preferred because it provides a smooth "feel" on the skin of the user. A variety of other crystalline shapes, such as needles, rhomboids, etc., have also been found to provide acceptable UV protection, however, and may be utilized in the formulations of the invention as well, although as noted above, spherical particles are the most preferred. On the basis of the optical properties of the substantially pure micronized zinc oxide particles developed by applicants, sunscreen products formed with this material remain visibly transparent on the skin while attenuating a greater portion of the UVA and UVB radiation than was previously possible with the use of prior art sunblock compositions, without resulting in any adverse effects caused due to transdermal absorption. This result is not possible with the only other commonly used metal oxide, i.e., titanium dioxide, due to the different, i.e., less effective, optical properties exhibited by titanium dioxide.

Another embodiment of the present invention is directed to the formation of physical sunscreen products comprising a particulate zinc oxide sunblock, preferably spherical in shape, having a diameter of an order of magnitude greater than the "standard size" (i.e., 0.01–0.9μ) particles used in prior art sunscreen compositions described above. The particles used in the subject embodiment are thus also substantially larger than the micronized particles described for use with the previous embodiment, i.e., they measure at least about 1 micron, and preferable between about 1–100 microns in diameter. At diameters above about 100μ, the optical performance of this material appears to deteriorate somewhat.

What is required, however, is that these particles be prepared by a process, such as gas phase chemical vapor deposition (CVD), spray pyrolysis or sol-gel particle formation, which results in the formation of symmetrical, substantially "optically perfect" crystals which are essentially free of internal fractures and/or other physical imperfections, and which have a relatively smooth outer surface. Such crystals, as a result of their morphology, have the required optical properties for use with the sunscreen formulations of the present invention, i.e., they attenuate a substantial portion of the ultraviolet radiation to which, they are exposed, which, as noted above, is greater than that which is attenuated with the use of prior art sunblock products, while remaining transparent in the range of visible wavelengths.

In addition, the relatively large crystals of the subject embodiment are also substantially pure as described above and thus contain only insignificant amounts of the trace metals listed in Table I below. The "purity" of these particles renders sunscreen formulations containing this sunblock material suitable for topical application to human skin without danger due to transdermal absorption of trace metals. The substantially pure zinc oxide particles are incorporated into a liquid carrier, such as the emulsion described above, to form a visibly transparent sunscreen formulation capable of attenuating a substantial portion, if not all, of the ultraviolet radiation directed upon the skin of the user to which this material is applied.

Alternately, in a further embodiment, particles of a visibly transparent UV-attenuating glass may be substituted within the emulsion for the zinc oxide particles described above. The glass particles used in the subject embodiment have an average diameter ranging between about 0.01–100 microns. They must also possess a relatively smooth outer surface and be substantially free of internal fractures or other physical imperfections. One well-known optical glass composition which has been shown to provide the desired results is referred to as Corning BK-7 (i.e., borosilicate crown-7) glass. The formulation of this material is well known and thus need not be described herein.

A still further embodiment of the present invention comprises a physical sunscreen formed with a plurality of small, visibly clear or colored plastic spheres measuring between about 0.01–100 microns in diameter. To obtain the proper optical performances, one or more UV-attenuating compounds, which may be chosen from a variety of materials well known in the art, are incorporated into the plastic used to form these spheres. The UV-attenuating compound, once incorporated into the plastic spheres, has reduced potential to react with or be absorbed by the skin. These UV-attenuating spheres are then dispersed in a liquid vehicle, such as the emulsion discussed above, to form a visibly transparent sunscreen lotion which may be topically applied to prevent ultraviolet radiation from reaching the skin of the user.

All of the particulate materials described above for use in the sunscreen formulations of the present invention may also be incorporated by known blending methods into a variety of cosmetic products such as lipstick, eye-shadow, foundations, moisturizer, rouge and the like to form cosmetics having an increased ability to prevent damage to underlying skin by the action of solar UV radiation. In addition, coloring agents may be included in the formulations described herein. For example, a coloring agent may be added to a matrix material prior to formation of a particle comprising the matrix and a UV attenuator, such that the coloring agent is contained in the particle itself.

Alternatively, the coloring agent simply may be added to the plurality of particles after particle formation. Examples of coloring agents useful according to the invention include conventional cosmetic coloring agents such as various iron oxides, ferric or ferro cyanide blue, chromium oxide greens, and FD&C colorants.

DETAILED DESCRIPTION OF THE PREFERRED EMBODIMENTS

In selecting particulate materials for use in forming applicants' 1) sunscreen products, and 2) cosmetic formulations containing the sunblocking agents of the invention, three optical properties, i.e., the absorption, reflection and refraction of these materials must be considered.

With regard to the first of these properties, i.e., optical absorption, it will suffice to note that, for purposes of the present invention, this parameter is defined by a characteristic optical energy known as the "bandgap" energy. Semiconductor materials such as the metal oxides, the visibly transparent glasses (e.g., BK-7) and UV-attenuating plastics described herein are transparent to wavelengths above this bandgap value while they absorb energy having a wavelength lower than the bandgap energy. Thus it is preferred to use materials whose bandgap energies are such that they remain visibly transparent while attenuating wavelengths of light below about 400 nm, i.e., in the ultraviolet range.

Optical reflection and refraction are the remaining properties which must be taken into account in predicting the performance of the particulate materials chosen for use in the present invention. With regard to these properties, it is important to note, first, that the ability of a particle to reflect light is affected by the morphology of the surface of the material of which the particle is formed, by the angle of light incident to the surface of the material and by the difference in the index of refraction of the material compared to that of the surrounding media. That is, the closer the refractive index of the particulate material is to that of the medium in which it is suspended, the less visible contrast there will be. Formulation bases for use on human skin typically have a refractive index of no greater than about 1.6 while the refractive index of titanium dioxide is about 2.5 and that of zinc oxide is about 1.9.

Secondly, particles, i.e., crystals, formed with rough surfaces or having internal fractures or other physical imperfections will scatter incident light more than smooth particles and/or those lacking such fractures and imperfections. In some embodiments of the invention, it is thus preferred to use particles having a substantially smooth outer surface which are relatively free of internal fractures and imperfections in the present invention. This enables sunscreen products formed with these sunblock materials to attenuate a substantial portion of the UV wavelengths to which the user is exposed while remaining substantially transparent on the surface of the skin. After an extensive review of the literature in this field, applicants are aware of no teaching or suggestion to utilize zinc oxide particles of the type described herein in applications such as those contemplated by Applicants, namely as a component of: 1) transparent sunscreen formulations or 2) cosmetic compositions capable of providing an enhanced degree of protection from solar rays. Nor are Applicants aware of any teaching or suggestion in the art to use solvent-free encapsulated UV-attenuating agents in a sunscreen or cosmetic formula. Thus, the use of applicants' particles in the manner indicated provides totally unexpected results with regard to the ability of this material to protect the user against the effects of solar radiation containing UV wavelengths.

Suitable carriers for forming the emulsions described herein include SD alcohol, lanolin, glyceryl stearate, cocoa butter, sorbitan sesquioleate, propylene glycol, mineral oil, isopropyl myristate, petrolatum and acrylic polymers. Mixtures of two or more of these materials may also be used. These materials are known in the art as being "dermatologically suitable", i.e., they do not cause or promote adverse reactions upon the skin of the user.

The amount of the carrier need only be sufficient to provide a uniform dispersion of the particles when they are applied to the skin to ensure adequate coverage of the skin with the UV-attenuating material. The particulate material preferably comprises no more than about 20% by weight of the total emulsion and preferably between about 1–10% by weight thereof. The only real limit on the lower end of this concentration range is that a sufficient quantity of the particulate must be included to permit the formulation to attenuate the desired amount of UV light. Concentrations of less than about 1% by weight of the total composition may even be useful in some instances.

EXAMPLE I

For those embodiments of Applicants' invention in which zinc oxide is a featured component, the substantially pure zinc oxide of Applicants' invention, i.e., having a minimal trace metal content as set forth in Table I below, is preferred for use herein in order to take advantage of the abrupt transition which zinc oxide undergoes from reflector to absorber at a bandgap energy corresponding to a wavelength of about 385 nm, i.e., substantially at the border between the UV and the visible regions. This bandgap energy value is in marked contrast to that of titanium dioxide, which does not show the same sharp change in transmission upon entering the ultraviolet region (see, e.g., Brown, Harvey E., Zinc Oxide: Properties and Applications, pp. 11–12(1976).

One drawback to the use of this material, however, is that titanium dioxide absorbs neither as much UV-radiation nor transmits as much visible radiation as, for example, zinc oxide, which is utilized by applicants in the present invention (see, e.g., Brown, Harvey E., Zinc Oxide: Properties and Applications, pp. 11–12, FIGS. 2–4 (1976). Thus, although the use of micronized titanium dioxide particles does render the resultant product smoother and less occlusive, it does not obviate the main drawback faced with the use of this material, i.e., its comparatively lower effectiveness (in contrast to ZnO) as a sunblock agent. Titanium dioxide-based products are also more opaque than those formed with the zinc-oxide of the present invention, which is due to the fact that the crystalline structure of the titanium dioxide material renders it only partially transparent to visible wavelengths of light and thus not generally as acceptable for cosmetic use.

Although it has been known to form micronized particles of zinc oxide for very specialized uses in the rubber industry, those particles contain substantial quantities (i.e., greater than about 200 ppm) of trace metals such as lead, mercury, arsenic and cadmium. The potential dangers to human health caused by exposure to these materials is well-documented. Thus, such zinc oxide particles containing these levels of trace metals are not acceptable for topical application to human skin.

A further advantage to the use of zinc oxide over titanium dioxide in some of the sunblock formulations of the present invention is that zinc oxide is substantially less expensive than titanium dioxide, thus providing a significant cost savings with the use of this material in applicants' invention. Still further, as noted above, applicants' substantially pure micronized zinc oxide particles contain a substantially lower amount of trace metals than is typically found in the specialty purpose micronized particles of this material. The use of such prior art micronized zinc oxide is, as discussed above, not possible because of the toxicity of this material due to the relatively high concentrations of trace metals contained therein.

Applicants have discovered, with respect to one embodiment of the present invention, that their substantially pure micronized particles of zinc oxide (described below), when dispersed in a dermatologically suitable liquid carrier in the form of a colorless emulsion, form a visibly transparent sunscreen when applied to human skin. As used herein, "visibly transparent" refers to the optical property of visual transparency when the formula is applied in a thin film (i.e., <100 microns, preferably <20–50 microns). This formulation is capable of attenuating a substantial quantity, if not all, of the UV radiation to which the user is exposed. As noted above, these zinc oxide particles are preferably spherical in shape to provide a "smooth" feel to the product and to facilitate its application onto the skin, but non-spherical particles, such as needles, squares, rhomboids, etc., may also serve the required purpose, although they are not as preferred.

Although, as noted above, micronized particles of zinc oxide are known in the art for specialty applications in the rubber industry, such particles contain elevated levels, i.e., greater than 200 ppm, of toxic trace metal contaminants. These trace metals include lead, cadmium, mercury and arsenic, all of which are known to be hazardous to human health. In contrast, the "substantially pure" zinc oxide particles developed by applicants for use in the present invention, whether in the form of micronized particles or as larger, "optically perfect" particles as described above, contain no more than the following ranges of the trace metals listed below.

TABLE I

| Lead | <20 ppm |
|---|---|
| Arsenic | <3 ppm |
| Cadmium | <15 ppm |
| Mercury | <1 ppm |

EXAMPLE II

Another embodiment of the applicants' sunblock formulations comprises substantially pure particles of zinc oxide, preferably spherical in shape, having a diameter substantially greater by at least an order of magnitude than the "standard" sized zinc oxide particles used with prior art sunscreen compositions described above and about two orders of magnitude greater than the micronized zinc oxide particles. Thus, the zinc oxide particles preferred for use in the subject embodiment of the invention measure at least about 1 micron in diameter, and preferably between about 5–20 microns. The upper end of this range is not critical, however, and thus the subject particles may range up to 50 or even 100 microns in diameter. Furthermore, the particles need not be spherical, although that shape is preferred since it facilitates application of the sunblock composition onto the skin when the zinc oxide particles are dispersed in a liquid carrier such as the emulsion discussed above. The concentration of these particles within the emulsions is essentially the same as that used for the embodiment utilizing micronized zinc oxide, i.e., between about 1–10% by weight.

As noted above, the bandgap energy value of zinc oxide is such that it changes from transparent to opaque at approximately the border between visible and UV light. However, as previously discussed, if the zinc oxide particles have rough surfaces or if they have internal fractures or other physical imperfections, these features will contribute to the scattering of incident light and a sunscreen product formed of such a material will thus not be visibly transparent.

In order to overcome these difficulties, the substantially pure zinc oxide particles of the subject embodiment are preferably formed with the use of a chemical vapor deposition ("CVD") technique, which results in the formation of symmetrical particles of zinc oxide having a diameter within the range noted above, which appear visibly clear upon the surface of the skin while remaining capable of attenuating a substantial portion of the UV radiation to which they are exposed. These particles are thus considered by applicants to be substantially "optically perfect" for the purposes of their invention.

In the CVD process used with the present invention, zinc source compositions are introduced as vapors into a heated reaction volume, i.e., chamber, where they react with oxygen, typically supplied as a gas, to form the zinc oxide particles described above, i.e., ranging in size from about 1 to about 100 microns. The driving force for this reaction can be the exothermic formation energy of the zinc oxide product itself or this energy may instead be supplied by external sources such as thermal or radio frequency (RF) plasma energy. The entire process may be automated and computer controlled in a manner known in the art.

More specifically, the CVD process utilized by applicants may utilize, as a zinc source, compositions such as zinc acetate, zinc chloride, zinc oxalate or organometallic zinc compounds such as dimethyl zinc ("DMZ") and diethyl zinc ("DEZ"). Applicants have determined that zinc oxide formed with the use of CVD from an organometallic zinc source will achieve particles having high growth rates at relatively low growth temperatures, i.e., below 500° C. and are thus preferred. The zinc sources used are thus preferably DMZ and DEZ, whereas the oxidating gas may be selected from among gaseous water, oxygen and alcohol.

Since both DEZ and DMZ are liquids, they are contained, prior to use, in a conventional bubbler device, typically maintained at about 20° C., whereupon they are subsequently transferred to the reactor via a carrier gas such as nitrogen or argon which is bubbled through the liquid. Water vapor is introduced to the reactor in a similar manner. The zinc and oxidizer source chemicals are injected into the hot reaction chamber through separate nozzles where they mix and react to form the zinc oxide particles. The ratio of oxidizing gas to the organometallic zinc should be greater than about 7:1, preferably about 10:1, in order to completely oxidize the zinc. The reaction temperature may range from about 180° to about 500° C., with the preferred range being from about 300° to 400° C. The reaction pressure can range from 1 torr to about 760 torr. For purposes of simplifying the apparatus, however, atmospheric pressure is preferred.

The desired zinc oxide particle size is achieved by (1) manipulating the amount of reactants used by, for example, a mass flow-controller, and (2) the residence time of these materials in the reactor. The relationship between these parameters is such that, for example, increasing the amount of time the reactants spend in the reaction chamber will result in a proportional size increase in the zinc oxide particles, having a diameter ranging in size from about 1–100 microns, are formed with a substantially smooth outer surface and, in addition, are substantially free of internal fractures and/or other physical imperfections. Moreover, if desired, an antireflection coating of, for example, silicon oxide may be applied to the surface of these particles to reduce the optical reflection from the material/media interfaces which thus renders them even more transparent to visible light.

Alternately, in place of the CVD process described above, acceptable zinc oxide particles may be formed with the use of other conventional processed such as spray pyrolysis (see, e.g., Eberspacher et al., "Pyrolysis of ZnO Film Deposited Onto InP By Spray Pyrolysis," Thin Solid Films, 136 (1986, pp 1–10) or sol-gel particle formation, both of which are well known to those skilled in the art.

Moreover, it is important to note that although zinc oxide and other metal oxide compositions have previously been commercially utilized in the form of relatively thick visibly transparent layers used, for example, in forming heat mirrors in architectural applications and as transparent electrical conductors for solar electric applications, the present invention is directed to the formation and use of separate, dispersed substantially pure zinc oxide particles in a liquid carrier to serve as a visibly transparent, UV-attenuating sunblock. Moreover, the inclusion of such relatively "optically perfect" visibly transparent, UV-attenuating particles of zinc oxide in sunscreen compositions of the type described herein has not, to applicants' knowledge, been contemplated anywhere in the prior art.

EXAMPLE III

In a further embodiment of the invention, particles of a visibly transparent glass having a bandgap energy at about 400 nm, thus permitting it to attenuate UV light while remaining virtually transparent to visible light, may be dispersed in the carrier in place of the 1–100μ zinc oxide particles described above. The diameter of the glass particles preferred for use in the invention may range between about 0.01–100 microns. In addition, these glass particles must have a substantially smooth outer surface and be substantially free of internal fractures and other imperfections. Any such optical glass meeting the requirements set forth above may be utilized, although borosilicate glasses such as the visibly transparent Corning BK-7 material described above are preferred for use with the present invention. The entirereflective coatings described above may also be used to coat the optically active glass particles of the type described herein.

EXAMPLE IV

Another embodiment of the invention comprises a sunscreen lotion including a plurality of commercially available plastic particles preferably, although not necessarily, spherical in shape with a diameter ranging between about 0.01–100μ, formed, in part, of a visibly transparent plastic. Such plastics are well-known in the art and may include, for example, acrylics such as polymethyl methacrylate ("PMMA"); styrene polymers; copolymers of styrene and acrylic; styrene acrylonitrile ("SAN"); polycarbonate; methylpentene; terpolymers of acrylontirile, butadiene and styrene ("ABS") and allyl diglycol carbonate ("ADC"). The invention should not, however, be limited to the use of these plastics, as any visibly transparent plastic having, or capable of being modified to have, as described below, the desired optical properties to render it visibly transparent but capable of attenuating UV radiation, is suitable for use in the present invention.

In order to control the UV attenuating properties of these plastics, one or more UV absorption additives, also known as "UV stabilizers", may be incorporated into the plastic used to produce the spheres during their formulation. Although it has been previously known in the art to add UV stabilizers to plastic substrates, such as in the formation of large sheets of UV-absorbent plastic, the incorporation of such UV stabilizers into small plastic spheres of the type described herein has not been previously known for use in sunscreen applications.

EXAMPLE V

Yet another embodiment of the invention comprises a sunscreen lotion including a sunscreen component comprising a plurality of sunscreen-encapsulated particles preferably, although not necessarily, spherical in shape with a diameter ranging between about 0.01–100μ, formed, in part, of a visibly transparent or a colored capsule matrix. Matrices useful for encapsulation according to the invention have general properties, as follows. Such matrices can be rendered water-dispersible; are relatively chemically inert, i.e., will not react with other sunscreen formula ingredients; are able to form a water-tight capsule such that sunscreen formula ingredients cannot enter the capsule; are able to resist degradation by and thus to hold an organic or inorganic compound in its interior; and may also possess improved tactile qualities in admixture with a sunscreen emulsion. In addition, certain preferred matrices may possess the following characteristics: i.e., a preferred matrix is preferably essentially non-water soluble (i.e., <5%); has a melting point preferably below 100 but not above 200 degrees Centigrade; and has a viscosity of less than 500 cp. at a temperature less than 100 degrees Centigrade. Any material that does not possess these characteristics alone may be combined with another material to produce a mixture having all of these characteristics. Preferred matrices have desirable qualities such as UV- or IR-attenuation properties.

Examples of encapsulating matrices useful according to the invention include matrices that are combinable with a UV-attenuating sunscreen according to methods of manufacture that do not require solvents for formation of a capsule. Such solvent-free methods of manufacture involve formation of the encapsulated sunscreen by a melt process.

The matrices include wax matrices, as described below, as well as polymer matrices such as commercially accepted natural oils and their derivatives (i.e., hydrogenated or oxidized) and synthetic oils, and lipid and protein derivatives. Natural oils include but are not limited to plantderived oils, such as castor, soybean, sesame, safflower, wheat germ, etc.; synthetic oils include but are not limited to silicones, cyclomethicone, etc.

Other preferred matrices include but are not limited to materials that are encapsulators according to a solvent-free process, e.g., polymeric materials such as alkylated vinyl pyrrolidone polymers (e.g., $C_{20}$–$C_{30}$); long chain (e.g., $C_{14}$–$C_{50}$, preferably $C_{20}$–$C_{30}$) alcohols; long chain ($C_{14}$–$C_{30}$) fatty acids; propylene glycol ester of fatty acids; ethene homopolymers (e.g., mw>400 g/mole); various grades of polymerized alkenes and alpha alkenes with molecular weights greater than 100 g/mole; ethylene-acrylic acid copolymers (Allied Signal AC 400 series); and ethylene-vinyl acetate copolymers (Allied Signal AC 400 series).

The invention should not, however, be limited to the use of these matrices, as any encapsulating matrix having, or capable of being modified to have, as described below, the desired optical properties to render the encapsulated UV-attenuator capable of attenuating UV radiation, yet dispersible in water, is suitable for use in the present invention.

The matrices described herein are not by nature dispersible to form a stable dispersion in water. Therefore, the invention includes the use of surfactants, e.g., anionic, nonionic, or cationic, or combinations thereof, to provide a useful degree of emulsification and consequent stability of the resulting particles. Surfactants useful in the invention will be of the type commonly used in the cosmetic industry, i.e., cosmetically acceptable. Examples of acceptable surfactants are provided in McCutcheon's Catalog of Emulsifiers and Detergents, MC Publishing, New York, Vol. 2, 1993, the contents of which are hereby incorporated by reference.

In order to control the UV absorbance properties of an encapsulating matrix according to the invention, one or more UV attenuating additives, also known as "UV stabilizers", may be incorporated into the matrix used to produce the particles during their formulation. The incorporation of such UV stabilizers into matrices of the type described herein according to solvent free processes has not been previously known for use in sunscreen applications.

UV additives are well known in the art (see, e.g., Modern Plastic Encyclopedia 1976–1977, pp. 222–227 and 708–709 and U.S. Pat. No. 4,882,143 to Kadokura et al., col. 7 lines 61–65) and include materials such as derivatives of salicylic acid, benzoic acid, cinnamic acid and benzophenone, benzotriazoles aryl esters, substituted acrylonitrile, metallic complexes and inorganic pigments. The invention should not be limited to the use of these specific materials, however, since any UV additive which serves the intended purpose, i.e., attenuating ultraviolet radiation, can be used with the formulations described with regard to the subject embodiment of the invention.

A sunscreen component of the invention will include particles of a visibly transparent or colored matrix and a UV-attenuating agent which may be made according to any solvent-free method that is known in the art (e.g., see Slivka, 1975, Chem. Internat. Ed. 14:539), including spray-drying (see, e.g., Brenner, Perfum. Flavour, 8:40, 1983), and coacervation, e.g., the conventional gelatin/gum arabic method (Bungenberg de Jong, in "Colloid Science", Vol. 2, H. R. Kruyt ed., Elsevier, Amsterdam, p.244, 1949, and U.S. Pat. No. 2,800,457), all of the above references of which are incorporated by reference. These methods may result in particles that are larger than desired, in which case modifications of other solvent-free methods may be preferred, e.g., melt-chill encapsulation, described in U.S. Pat. No. 3,865,799, herein incorporated by reference.

The melt-chill encapsulation method disclosed in U.S. Pat. No. 3,865,799 may be modified and thus improved to allow for production of particles having a diameter range that is smaller than the 20–500 micron diameter range particle described in U.S. Pat. No. 3,865,799. For example, one such improved method that is particularly useful for matrix materials such as waxes involves combining the molten encapsulating matrix material with a pre-heated aqueous phase to delay immediate formation of relatively larger particles that form as a result of combining molten material with a cool aqueous phase, as described in the prior art. This delay of particle formation allows for increased control over particle size, the control being enhanced by the use of surfactants in the process. This and other improvements are described below.

The matrix material, e.g., at a concentration of 1–50% of the formulation, is combined with one or more UV-attenuators, e.g., at a final concentration of 1–20%. The mixture is heated to a temperature required to melt and liquify all materials. The combination is then mixed to provide a homogeneous oil phase. The oil phase may also contain oil-soluble surfactants, e.g., at a concentration of 0.1–10%. A quantity of water, e.g., 40–90% of final formulation, is separately heated to the same or a higher temperature as the oil phase, the temperature preferably does not exceed 100 degrees centigrade. The water phase may contain water-soluble surfactants, e.g., at concentrations within the range 0.1–10%. Maintaining temperature, the oil phase is emulsified into the water phase using a high speed mixer, colloid mill, homogenizer, or ultrasonic processor. Once the emulsification is complete, the resultant fluid is cooled to room temperature. Cooling results in solidification into discrete small particles of emulsion droplets of molten matrix and UV-attenuator materials, the particles being dispersed in an aqueous continuous phase.

Alternatively, the above-described melt-chill process is modified by heating the matrix material to melting temperature and then combining the liquified matrix material with a solid particulate UV-attenuator. The UV-attenuator may be dispersed in the liquified matrix material using a high speed mixer, colloid mill, homogenizer, or ultrasonic processor. The oil phase may also contain oil-soluble surfactants, e.g., at a concentration of 0.1–10% to enhance the degree of dispersion of particulate material and/or emulsification. A quantity of heated water is added, and the oil phase emulsified into the water phase as above. Once emulsification is complete, the resultant fluid is cooled to room temperature. Upon cooling, droplets of the emulsion solidify into discrete small particles which are dispersible in an aqueous continuous phase.

It also will be understood that the above-described processes may be modified (1) to allow for two or more UV-attenuators to be combined in the same particle; and (2) to allow for two or more types of matrix materials to be combined in a particle.

Additional improvements that have been discovered for the above-described improved melt-chill process are as follows. In the case of organic sunscreen material, especially solid crystalline materials, solubilizing materials, such as those found in McCutcheons Catalog of Functional Materials, 1993, pp. 238–248, may be included in the particles to increase the solubility of the crystalline materials in the particles, thereby reducing the potential of the sunscreen material to recrystallize in or from the particles. This is especially true for those materials that occur as highly acicular crystals; acicular shapes have a strong thermodynamic tendency to exist in crystal form. Useful solubilizers will be good solvents for the UV attenuating compound(s) and will have little and preferably no water solubility.

In the case of inorganic particulate materials, an improvement of the melt-chill process involves pretreatment of the inorganic particulates with a hydrophobic compound such as silane. Silane covalently binds to the surface of the particles and converts inherently hydrophilic inorganic oxides to a hydrophobic state. It has been discovered that pretreating these inorganic agents with a hydrophobic compound increases the degree of dispersion of the inorganic particles within the matrix. This pretreatment improves both final particle size as well as completeness of encapsulation, and thus also improves isolation of these materials from ambient conditions. Silane hydrophobing compounds can be applied to the inorganic oxide particulates either by vapor treatment or from solution.

Wax matrices useful according to the invention include, but are not limited to, natural and synthetic waxes that contain mixtures of alkyl wax esters, resins, and other vegetable matter components; clay-treated microcrystalline waxes; oxidized hydrocarbon waxes; natural and synthetic beeswax, auto-oxidized beeswax, candelilla, carnauba, and synthetic waxes prepared by esterification of natural plant-derived fatty acids and alcohols; various grades of paraffin waxes; and matrices including lipids, proteins, and their derivatives. Other materials included herein as examples of waxes, comprise, e.g., polymeric materials such as alkylated vinyl pyrrolidone polymers; long chain alcohols; long chain carboxylic acids; propylene glycol ester of fatty acids; ethene homopolymers; various grades of polymerized alkenes and alpha alkenes with molecular weights greater than 100 g/mole; ethylene-acrylic acid copolymers; and ethylene-vinyl acetate copolymers.

Provided below are examples of improved melt-chill processes according to the invention. The process is selected depending upon the physical and chemical characteristics of the UV attenuating material to be encapsulated.

EXAMPLE VI

For liquid organic UV attenuating materials, 5 gms of the organic UV attenuating material Escalol 557 (Octyl Methoxy Cinnamate-ISP Van Dyke) is combined with 5 gms carnauba wax (Koster Keunen). The combination is heated to 90 degrees centigrade to form a liquid state and mixed to homogenity. Separately, 90 gms of deionized water is combined with 4 gms of the nonionic emulsifier polyoxyethylene (23) lauryl ether (Brij 35-ICI Americas) and also heated to 90 degrees centigrade. The two phases are combined, maintaining temperature, and emulsified using a high speed mixer (Omni 5100 mixer, Omni International, Gainsville, Va., with a 10 mm diameter generator probe, at a setting of 8) for 5 minutes. The resulting emulsion is then allowed to cool with stirring to room temperature in order to solidify the emulsion droplets of OMC and carnauba wax into discrete particles. The resulting OMC concentration is around 5% which can be increased by evaporation of the water continuous phase.

EXAMPLE VII

For solid organic UV attenuating material with solubilizer, 5 gms of the organic UV attenuating material Escalol 567 (benzophenone-3-ISP Van Dyke) is combined with 15 gms of the solubilizer Ceraphyl 368 (octyl palmitate-ISP Van Dyke) as well as 20 gms of carnauba wax (Koster Keunen). The combination is heated to 90 degrees centigrade to dissolve the benzophenone-3, form a liquid state, and mixed to homogenity. Separately, 60 gms of deionized water is combined with 5 gms of the nonionic emulsifier polyoxyethylene (23) lauryl ether (Brij 35-ICI Americas) and also heated to 90 degrees centigrade. The two phases are combined, maintaining temperature, and emulsified using a high speed mixer (as in Example VI) for 5 minutes. The resulting emulsion droplets of octyl palmirate and carnauba wax matrix and benzophenone-3 into discrete particles. The resulting benzophenone-3 concentration is around 5% which can be increased by evaporation of the water continuous phase.

EXAMPLE VIII

For solid inorganic particulate UV attenuating material, 15 gms of Polywax 500 (polyethylene wax-Petrolite) and 1 gm of the oil soluble nonionic dispersant Capmul GMO (glyceryl mono/dioleate-Karlshammus U.S.A.) are combined and heated to 90 degrees centigrade to form a liquid state, and mixed to homogenity. To this melted liquid is added 5 gms of the inorganic particulate UV attenuating material Z-cote (microfine zinc oxide, sunSmart, Inc, New York). The entire mixture is processed with an ultrasonic processor for 2 minutes in order to disperse the zinc oxide particulate material. Separately, 80 gms of deionized water is combined with 5 gms of the nonionic emulsifier polyoxyethylene (23) lauryl ether (Brij 35-ICI Americas) and also heated to 90 degrees centigrade. The two phases are combined, maintaining temperature, and emulsified using a high speed mixer (as in Example VI) for 2 minutes, followed by 1 minute using and ultrasonic processor. The resulting emulsion is then allowed to cool with stirring to room temperature in order to solidify the emulsion droplets of polyethylene wax matrix containing particulates of the zinc oxide, into discrete particles. The resulting zinc oxide concentration is around 5% which can be increased by allowing the hardened particles to settle, due to their high density, followed by decanting off a portion of the water continuous phase.

Some of the particles described herein, i.e., those particles formed from conventional high melting point plastics produced by solvent-emulsification methods of manufacture or emulsification polymerization processes, inherently contain solvent or monomer residuals which are by nature toxic, highly irritating, or sensitizing to human skin. However, the particle component of encapsulated sunscreens of the invention are easy to manufacture in that a capsule matrix may be chosen that is amenable to preparation by less toxic methods of manufacture; for example, a wax matrix can be melted using conventional "melt-chill" methods known in the art, thus eliminating the need for organic solvents. In addition, the products achieved via such methods of manufacture are less toxic, an important consideration for agents applied to the skin.

Many excellent sunscreens are organic and water-insoluble, and thus are not compatible with water-based sunscreen formulae. Water-based sunscreens are often preferred over oil-based sunscreens by virtue of their lower cost and certain aesthetic considerations, e.g., less greasiness. Encapsulation of a sunscreen agent in an inert wax capsule converts an oil-soluble sunscreen agent into a water-dispersible agent. For example, the oil-soluble common organic sunscreen octyl methoxycinnamate (OMC) was encapsulated in an accepted cosmetic wax, carnauba, at a ratio of one part OMC to one part carnauba wax. The OMC/carnauba wax particles were then modified with an aqueous gel of carbopol polymaer, an aqueous soluble polymer of polyacrylic acid (BF Goodrich, Inc.), at a resultant active concentration of 5% OMC. It is to be noted that this simple formulation contains no additional cosmetic oil normally needed to formulate a sunscreen with OMC. The sun protection factor (SPF) of the resultant sunscreen formula was determined by FDA approved methods on five subjects, and was 8.2, as shown in Table 1.

Inorganic sunscreen agents that may by nature be dispersible in either of the oil or water phases of a conventional cosmetic formulation are normally placed in oil in order to attempt to provide some degree of waterproofness to the particulate inorganic UV attenuating agent. This invention, by the use of film-forming matrix materials for encapsulation (i.e., that bind to the skin to provide waterproofness) eliminates the need to include the agent in an oil phase, thereby increasing the options for the cosmetic formulator in providing a waterproof sunscreen formulation.

Encapsulation of sunscreen agents also allows for minimization of undesirable chemical reactions between the sunscreen and other active ingredients in the sunscreen formula. For example, some sunscreens, such as benzophenone, are known to form crystals in solution. However, wax-encapsulated benzophenone did not crystallize in solution. Thus, encapsulation of this organic compound prevented its crystallization in solution.

Encapsulation of sunscreen agents allows for control of ambient conditions around the sunscreen component particles. Thus, the invention allows combining of sunscreen agents which when unencapsulated are chemically reactive such that they lose their UV-attenuating properties when combined, or cause other adverse reactions such as discoloration. Individual encapsulation of chemically reactive sunscreen agents allows the formulator to disregard these chemical reactivities, and to choose admixtures of any number of sunscreen agents.

The inclusion of additive materials into the plastic spheres or encapsulating matrices described above serves to render these visibly transparent or colored particles capable of attenuating UV radiation. Thus, upon dispersing these transparent, UV-attenuating particles in a liquid carrier such as the emulsion described with reference to the embodiment of the invention utilizing substantially pure particles of micronized zinc oxide, in a concentration ranging between about 1-20% by weight of the emulsion and, more preferably, between about 1-10% by weight, the resultant formulation may be topically applied onto the skin of the user, whereupon it remains visibly transparent or colored while attenuating a substantial portion of the UV radiation to which the user is exposed.

Moreover, the particulate sunblock materials described above for inclusion in the topical sunscreen formulations of the present invention may, in still further embodiments of the invention, be incorporated into a variety of cosmetic products such as, for example, lipstick, eyeshadow, foundations, moisturizers, rouge, hair products such as shampoos and conditioners, and other personal care products to enhance the ability of these formulations to protect the underlying skin of the user from the damaging effects of UV radiation. These materials may be blended with the cosmetic base by known blending methods such as by means of Henschel mixer, a ribbon mixer, a twin-cylinder mixer or the like.

The amount of such particulate material present within the cosmetic formulations of the invention comprises no more than about 40% by weight, and preferably between about 1-20% by weight.

The cosmetic formulations described above may also contain a variety of additive materials. These additives are well-known in the art and are added for the purpose of performing their inherent functions. The preferred additives include materials such as thickeners, softeners, superfatting agents, waterproofing agents, emollients, wetting agents and surface-active agents, as well as preservatives, anti-foam agents, perfumes and mixture thereof, or any other compatible ingredient usually employed in cosmetics.

While it is apparent that the invention herein disclosed is well calculated to fulfill the objects above stated, it will be appreciated that numerous modifications and embodiments may be devised by those skilled in the art and it is intended that the appended claims cover all such modifications and embodiments as fall within the true spirit and scope of the present invention.

We claim:

1. A component of a sunblock formula, comprising a plurality of particles having diameters in the size range of about 0.01-100 microns and comprising a matrix in combination with a UV-attenuating compound, said plurality of particles being solvent-free and dispersible within a dermatologically acceptable carrier.

2. A component of a sunblock formula, comprising a plurality of particles having diameters in the size range of about 0.01-100 microns formed from a matrix comprising wax and a UV-attenuating compound incorporated into said wax, said particles being solvent-free and dispersible within a dermatologically acceptable liquid carrier.

3. The component of claim 1 or 2, said particles comprising a coloring agent.

4. The component of claim 1 or 2 wherein said plurality of particles further comprises a second UV-attenuating compound that is incorporated into said matrix.

5. The component of claim 1 or 2 wherein said plurality of particles comprises a first UV-attenuating compound and a second UV-attenuating compound that are individually incorporated into said matrix to form separately encapsulated first and second UV-attenuating compounds.

6. The component of claim 1, said matrix comprising a material selected from the group consisting of: vinyl pyrrolidone polymer; long chain alcohol; long chain carboxylic acid; propylene glycol ester of fatty acid; ethene homopolymer; polymerized alkene and alpha alkene having a molecular weight greater than 100 g/mole; ethylene-acrylic acid copolymer; and ethylene-vinyl acetate copolymer.

7. The component of claim 2, said wax comprising a material selected from the group consisting of a natural and a synthetic wax.

8. The component of claim 7, said natural wax comprising a material selected from the group consisting of alkyl wax ester, resin, vegetable matter components, clay-treated microcrystalline wax, oxidized hydrocarbon wax, natural and synthetic beeswax, auto-oxidized beeswax, candelilla, and carnauba.

9. The component of claim 7, said synthetic wax comprising a material selected from the group consisting of synthetic wax prepared by esterification of natural plant-derived fatty acids and alcohols, and paraffin wax.

10. The component of claim 1 or 2, wherein said UV-attenuating compound is selected from the group consisting of organic and inorganic UV-attenuators.

11. The component of claim 10, said organic UV-attenuator being selected from the group consisting of benzophenone, cinnamate, salicylate, aminobenzoic acid ester, menthyl anthranilate, 2-ethylhexyl-2-cyano-3,3-diphenyl acrylate, 2-phenylbenzimidazole-5-sulfonic acid, digalloyl trioleate, 3-(4-methyl benzylidene) camphor, 4-isopropyl dibenzoyl methane, butyl methoxy dibenzoyl methane, 2-ethyl-2-cyano-3,3'-diphenyl acrylate.

12. The component of claim 10, said inorganic UV-attenuator being selected from the group consisting of a metallic complex and an inorganic pigment.

13. The component of claim 12, said metallic complex comprising zinc oxide.

14. A substantially transparent topical sunblock formula for shielding skin from ultraviolet radiation, said formula comprising an effective amount of the component of claim 1 or 2 dispersed within a dermatologically acceptable carrier in at least an amount sufficient to shield substantially all skin over which said formula is applied from hazardous effects of ultraviolet radiation.

15. A method of making a substantially transparent topical sunblock formula for shielding skin from ultraviolet radiation, comprising dispersing the sunscreen component of claim 1 or 2 in a dermatologically acceptable carrier in at least an amount sufficient to shield substantially all skin over which said formula is applied from hazardous effects of ultraviolet radiation.

16. A method of shielding the skin from ultraviolet radiation, comprising spreading an effective amount of the substantially transparent topical sunblock formula of claim 14 or 15 over the skin sufficient to shield substantially all skin over which said formula is applied from hazardous effects of ultraviolet radiation.

17. A method of preparing the component of claim 1 or 2, comprising subject said matrix and said UV-attenuating compound of claim 1 or 2 to a solvent-free process to produce a solvent-free plurality of particles comprising said matrix and said UV-attenuating compound.

18. A process for preparing a component of a sunscreen formula, comprising the steps of:

(a) heating an encapsulating matrix above its melting point at a temperature in the range of 30–200 degrees Centigrade for a time sufficient to form a liquified encapsulating matrix;

(b) mixing a UV attenuating compound with the liquified encapsulating matrix of step (a);

(c) emulsifying the mixture of step (b) with an aqueous medium comprising surfactant, said aqueous medium being at a temperature in the range of 30–200 degrees Centigrade; and (d) cooling the emulsion to room temperature, wherein the particles formed therefrom have diameters in the range of about 0.01–100 microns and comprise said matrix in combination with said UV-attenuating compound, said particles being solvent-free and dispersible within a dermatologically acceptable carrier.

19. The process of claim 18, wherein said temperature range of steps (a) and (c), individually, is 30–100 degrees Centigrade.

20. The process of claim 18, wherein said encapsulating matrix of step (a) comprises a substance selected from the group consisting of: natural wax and synthetic wax.

21. The process of claim 20, said natural wax comprising a material selected from the group consisting of alkyl wax ester, resin, vegetable matter components, clay-treated microcrystalline wax, oxidized hydrocarbon wax, natural and synthetic beeswax, auto-oxidized beeswax, candelilia, and carnauba.

22. The process of claim 20, said synthetic wax comprising a material selected from the group consisting of synthetic wax prepared by esterification of natural plant-derived fatty acids and alcohols, and paraffin wax.

23. The process of claim 20, wherein said UV-attenuating compound is selected from the group consisting of organic and inorganic UV-attenuators.

24. The process of claim 23, wherein said process further comprises the step of pretreating said inorganic UV-attenuator with a hydrophobic compound prior to mixing with said heated matrix.

25. The process of claim 23, wherein said process further comprises the step of mixing said organic sunscreen material with a solubilizing agent prior to incorporation into the matrix in an amount sufficient to reduce the potential of the UV-attenuator to recrystallize in the particle form.

* * * * *